(12) United States Patent
Theeraworn

(10) Patent No.: US 12,616,783 B2
(45) Date of Patent: May 5, 2026

(54) BREAST PUMP ADAPTER

(71) Applicant: Inteplast Group Corporation, Livingston, NJ (US)

(72) Inventor: Nuttikorn Theeraworn, Nongmaidan (TH)

(73) Assignee: INTEPLAST GROUP CORPORATION, Livingston, NJ (US)

( * ) Notice: Subject to any disclaimer, the term of this patent is extended or adjusted under 35 U.S.C. 154(b) by 215 days.

(21) Appl. No.: 17/647,617

(22) Filed: Jan. 11, 2022

(65) Prior Publication Data

US 2022/0218884 A1      Jul. 14, 2022

Related U.S. Application Data

(60) Provisional application No. 63/136,099, filed on Jan. 11, 2021.

(51) Int. Cl.
*A61M 1/06* (2006.01)

(52) U.S. Cl.
CPC .................................. *A61M 1/062* (2014.02)

(58) Field of Classification Search
CPC . A61J 9/005; A61J 11/04; A61J 11/045; A61J 9/06; A61J 1/10; A61M 1/06–069; B65D 75/5883
See application file for complete search history.

(56) References Cited

U.S. PATENT DOCUMENTS 4,718,778 A * 1/1988 Ichikawa ........... B65D 75/5883
                                                    220/705
4,850,496 A    7/1989 Rudell et al.

5,261,553 A    11/1993 Mueller et al.
5,758,787 A *   6/1998 Sheu ........................ A61J 11/04
                                                      215/11.1
6,000,848 A *  12/1999 Massioui ............. B65D 77/283
                                                     383/906
6,257,429 B1 *  7/2001 Kong ................... A61J 11/0005
                                                      215/388

(Continued)

FOREIGN PATENT DOCUMENTS

DE       202015104212 U1   12/2016

OTHER PUBLICATIONS

Medela, Inc., Pump & Save product sheet, 2 pages (C) 2012, Medela, Inc.

(Continued)

*Primary Examiner* — Courtney B Fredrickson
(74) *Attorney, Agent, or Firm* — Stinson LLP

(57) ABSTRACT

An adapter for connecting a breast milk collection bag to breast milk pump fittings of different sizes. A breast milk collection bag has an end margin configured to conform tightly over the adapter. The bag can have a reclosable seal. An adapter has a first adapter portion and a second adapter portion. The first adapter portion can connect to a fitting of a first breast milk pump of a first size. The second adapter portion can connect to a fitting of a second breast milk pump of a second size different from the first size. In another aspect, the adapter further has a retainer and a flow passage. The retainer is configured to engage and hold the end margin of the breast milk collection bag. The flow passage extends through the first adapter portion, the second adapter portion, and the retainer.

7 Claims, 9 Drawing Sheets

(56) References Cited

U.S. PATENT DOCUMENTS

| | | | |
|---|---|---|---|
| 6,575,202 | B2 | 6/2003 | Lafond |
| D486,224 | S | 2/2004 | Gay, III |
| D486,225 | S | 2/2004 | Gay, III |
| 6,962,439 | B2 | 11/2005 | Taheri |
| 6,991,121 | B1 | 1/2006 | Kipperman et al. |
| D633,797 | S | 3/2011 | Cresswell et al. |
| 8,357,116 | B2 | 1/2013 | Simdon |
| 8,579,874 | B1* | 11/2013 | Barack .................... A61M 1/06 |
| | | | 604/74 |
| D763,435 | S | 8/2016 | Patvibul et al. |
| 2002/0156419 | A1 | 10/2002 | Silver et al. |
| 2006/0074379 | A1 | 4/2006 | Hunt |
| 2007/0173756 | A1 | 7/2007 | Krebs et al. |
| 2008/0041859 | A1 | 2/2008 | Teglbjarg |
| 2009/0238495 | A1* | 9/2009 | Anderson ................ A61J 1/10 |
| | | | 383/7 |
| 2010/0262072 | A1 | 10/2010 | Attolini et al. |
| 2011/0098639 | A1 | 4/2011 | Kirchner |
| 2012/0022445 | A1 | 1/2012 | Jones |
| 2012/0041365 | A1 | 2/2012 | Simdon |
| 2012/0051670 | A1 | 3/2012 | Matias |
| 2014/0102918 | A1 | 4/2014 | Eitrheim et al. |
| 2014/0107608 | A1 | 4/2014 | McBean et al. |
| 2014/0213964 | A1 | 7/2014 | Taheri |
| 2014/0343486 | A1 | 11/2014 | Taheri |
| 2015/0024085 | A1 | 1/2015 | McBean et al. |
| 2015/0144584 | A1 | 5/2015 | Renz et al. |
| 2016/0003391 | A1* | 1/2016 | Okita .................... F16L 33/245 |
| | | | 285/382 |
| 2016/0015603 | A1 | 1/2016 | Mcbean et al. |
| 2016/0114090 | A1 | 4/2016 | Patvibul et al. |
| 2016/0287766 | A1 | 10/2016 | Bambino et al. |
| 2016/0317728 | A1 | 11/2016 | Lewis et al. |
| 2017/0021068 | A1 | 1/2017 | Gaskin et al. |
| 2018/0050183 | A1* | 2/2018 | Taylor .................. A61J 1/2037 |

OTHER PUBLICATIONS

Ameda, Store'N Pour(TM) Breast Milk Storage Bags, 2 pages, published at http://ameda.com/breastfeeding-products/milk-collection-storage/store'n-pour-breast-milk-storage-bags and archived by the "WayBackMachine" on Mar. 27, 2014.

Lansinoh, Pumping Directly into Lansinoh Breastmilk Storage Bags, Jul. 25, 2017, video published by Lansinoh Family via YouTube at https//www.youtube.com/watch?v=A7mYL0Mf6To.

Lansinoh, Pump Directly into our Breastmilk Storage Bags Using our Pump Adapter with your Breast Pump, Dec. 20, 2017, video published by LansinohUSA via YouTube at Https://youtube.com/watch?v=PA0KH1sSjuo.

* cited by examiner

BREAST PUMP ADAPTER

CROSS REFERENCE TO RELATED APPLICATIONS

The present application claims priority to U.S. Provisional Patent Application Ser. No. 63/136,099, entitled BREAST PUMP ADAPTER, the entire contents of which are hereby incorporated by reference.

FIELD OF THE DISCLOSURE

Aspects of the present disclosure relate generally to systems for filling a bag with liquid dispensed from the outlet of a breast pump. More specifically, aspects of the present disclosure relate to an adapter for securing a bag to breast pumps having different configurations.

BACKGROUND OF THE DISCLOSURE

Breast pumps are configured to pump breast milk into a receptacle. Conventional breast pumps attach to a plastic feeding bottle. The pumped milk is deposited directly into the feeding bottle. Certain breast pump systems are configured to pump directly into a flexible storage bag. Many of these systems require the bag to be contained in a rigid vessel during pumping. In some of the systems, the bag hangs directly from the pump or an adapter connected thereto. One adapter for securing a bag to a breast pump includes a conduit with diametrically opposite mounting hooks extending radially outward from the conduit. Each of the mounting hooks includes a radially outwardly projecting portion and an upwardly extending portion. To secure a bag to the adapter, holes in the bag are threaded over the upwardly extending portion of the mounting hooks and onto the radially outwardly projecting portion of the mounting hooks. The bag hangs down from the radially outwardly projecting portion of the mounting hooks during use. Since the mounting hooks in this design project radially outwardly from the conduit, the bag opening must be larger than the conduit so that the holes in the bag can be threaded onto the hooks. As a result, the bag does not closely conform to the conduit, which can permit air and contaminants to enter the bag. In addition, because the mounting hooks extend in two directions (i.e., radially outward and upward) removing the bag from the adapter when it is filled with liquid can be difficult. Moreover, the positioning of the adapter with the bag makes it impossible to seal the bag prior to removal of the bag from the adapter. Sealing the bag closed would prevent movement of the bag needed to remove the bag from the mounting hooks.

BRIEF SUMMARY OF THE INVENTION

In one aspect of the present invention, an adapter configured for connecting a breast milk collection bag to breast milk pump fittings of different sizes generally comprises a first adapter portion and a second adapter portion. The first adapter portion is configured for connecting to a fitting of a first breast milk pump of a first size. The second adapter portion is configured for connecting to a fitting of a second breast milk pump of a second size that is different from the first size.

In another aspect of the present invention, a breast milk pump adapter for connecting a breast milk collection bag to breast milk pump fittings of different sizes generally comprises a retainer, a first adapter portion, a second adapter portion, and a flow passage. The retainer is configured to engage and hold the breast milk collection bag on the adapter while the breast milk collection bag is filled with milk by the breast milk pump. The first adapter portion projects from a first surface of the retainer and is configured for connection to a fitting of a first breast milk pump of a first size. The second adapter portion projects from a second surface of the retainer opposite the first surface and is configured for connection to a fitting of a second breast milk pump of a second size that is different from the first size. The flow passage extends through the first adapter portion, the second adapter portion, and the retainer.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

The present disclosure improves upon the invention disclosed in co-assigned U.S. Pat. No. 9,931,450, and the contents of this patent are incorporated herein by reference.

Figure 1:
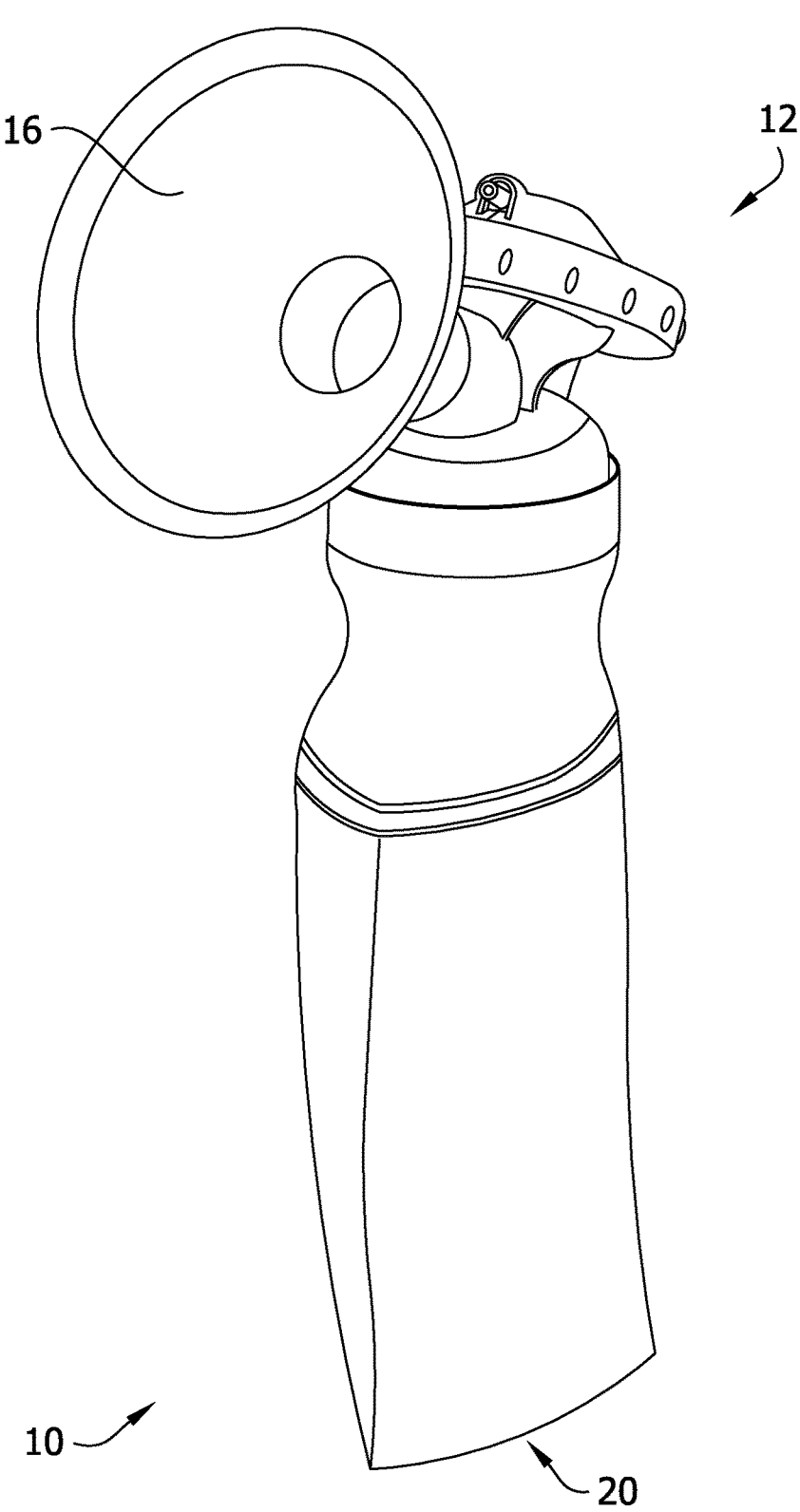
FIG. 1 is a perspective view of a breast pump system with a breast pump and a breast pump adapter.
Figure 2:
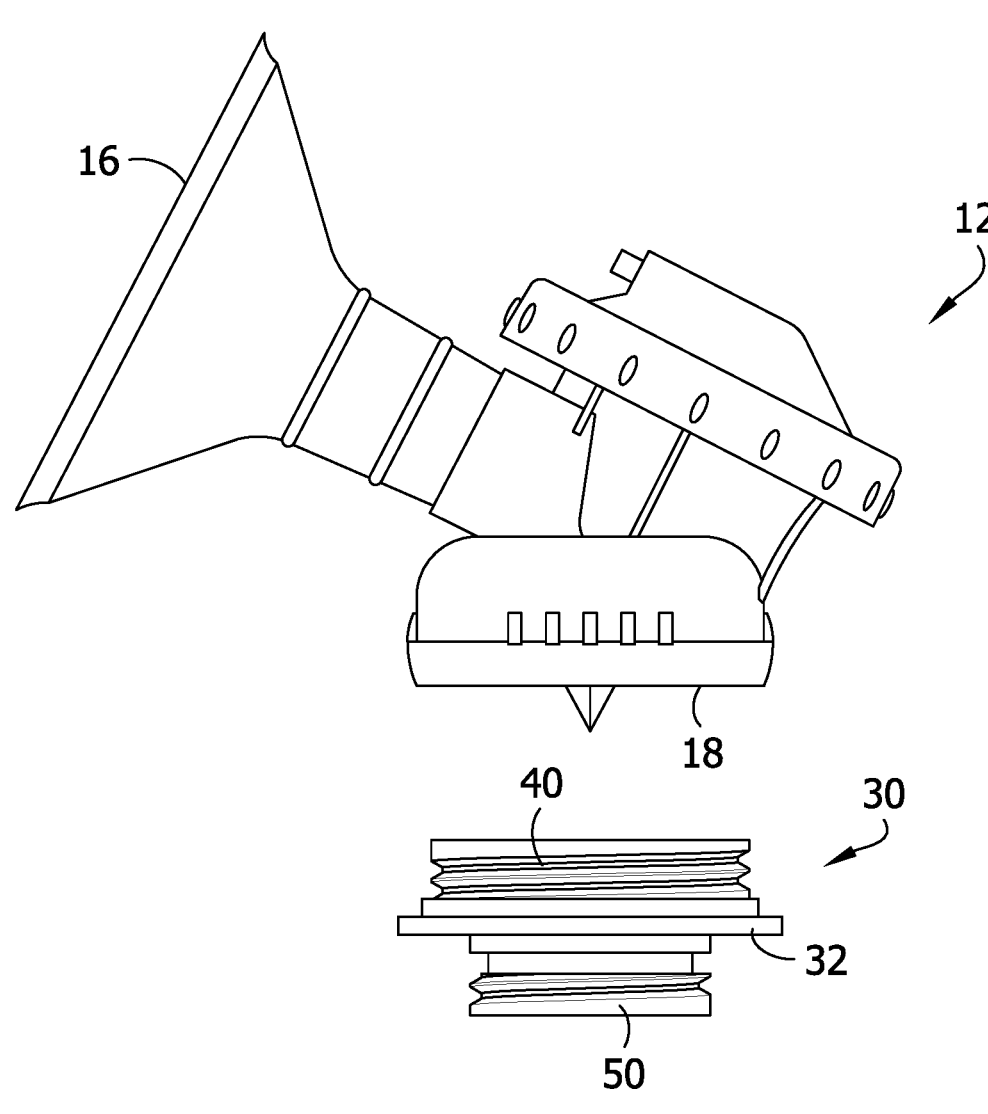
FIG. 2 is an elevation of a breast pump and an adapter from the breast pump system in which the adapter is detached from the breast pump.

Referring to FIGS. 1 and 2, a breast pump system is generally indicated at reference number 10. The breast pump system 10 includes a first breast pump 12, a flexible bag 20, and a breast pump adapter 30 for attaching the bag to the pump so that breast milk can be delivered into the bag. The first breast pump 12 has a fluid inlet portion 16 and a fluid outlet portion 18. The inlet portion 16 of the first breast pump 12 is configured to engage the breast of a user and pump breast milk (broadly liquid) into a receptacle, such as a bottle (not shown), the bag 20, or other suitable container. The outlet portion 18 of the first breast pump 12 is configured to thread into the threaded end of a first rigid plastic bottle (e.g., a baby bottle). The first breast pump 12 pumps liquid from the inlet portion 16 through the pump and dispenses the liquid out the outlet portion 18. As described in more detail below, the adapter 30 has a first adapter portion 40 that is configured to attach to the outlet portion 18 of the first breast pump 12 for attaching the bag 20 to allow liquid to be pumped in the bag. As is later described in more detail in connection with FIGS. 8-9, the breast pump adapter 30 can be used in in a second (inverted) configuration in an alternative breast pump system 10'. The alternative breast pump system 10' includes a second breast pump 12', the bag 20, and the adapter 30 in the inverted configuration. Like the first breast pump 12, the second breast pump 12' has a fluid inlet portion 16' and fluid outlet portion 18'. The outlet portion 18' of the second breast pump 12' is configured to thread into the threaded end of a second rigid plastic bottle with a smaller opening than that of the first bottle. As described in more detail below, the adapter 30 has a second adapter portion 50 (opposite the first adapter portion 40) that is configured to attach to the outlet portion 18' of the second breast pump 12' for attaching the bag 20 to allow liquid to be pumped in the bag.

Figure 3:
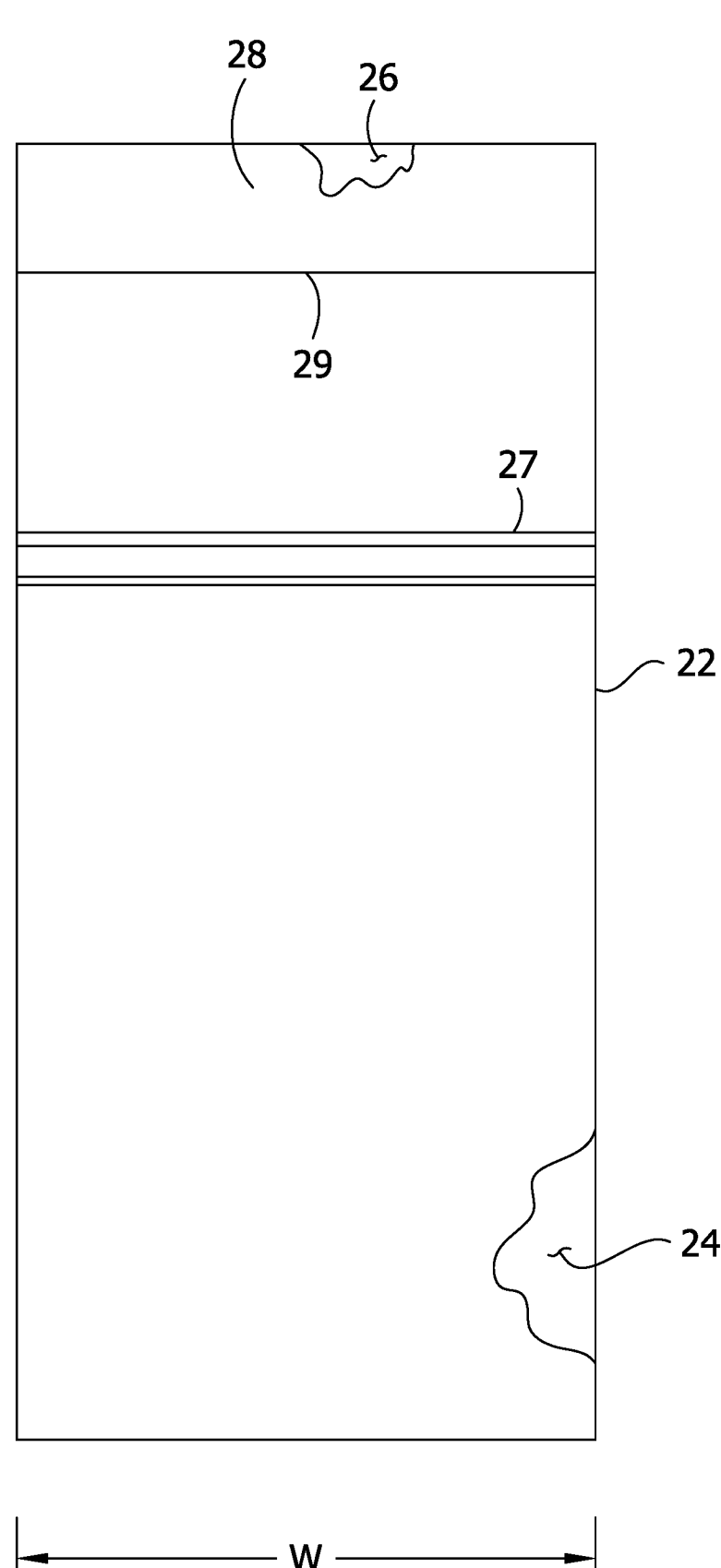
FIG. 3 is an elevation of a bag of the breast pump system with portions broken away.

Referring to FIG. 3, the bag 20 includes a bag body 22 defining a bag interior 24 and a bag opening 26. The bag body 22 can also include an end margin 28 adjacent the bag opening 26. The end margin 28 is configured for securing and hanging the bag 14 from the adapter 20. A reclosable seal 27 extends across a width W of the bag beneath the end margin 28. Though the illustrated bag 20 uses a reclosable seal, it is contemplated that other types of bags can use other types of seals or that a seal may be omitted without departing from the scope of the invention. In a preferred embodiment, a mark, such as the circumferential line 29 shown in FIG. 3, may be on the bag 20 to indicate to a user how far to pull the bag onto the adapter 30 for optimal use. For example, as is seen in FIG. 1, the line 29 can be aligned with the retainer rim 32 of the adapter 30. The bag 20 is constructed and arranged so that the bag does not tear under normal use while the bag is suspended from the adapter 30 and the bag interior 24 is filled with liquid. The bag 20 can also include additional or alternative features, including tamper resistance, easy opening seals, grip strips, dedicated labeling spaces, holes, or perforations.

Referring to FIGS. 1-2 and 4-7, the breast pump adapter 30 is configured to secure the bag 20 to the breast pump 12 to receive liquid dispensed through the outlet portion 18 of the breast pump into the bag interior 24. The adapter 30 includes a retainer rim 32, a first adapter portion 40 positioned above the retainer rim, and a second adapter portion 50 positioned beneath the retainer rim. A liquid flow passage 60 extends continuously through the first adapter portion 40, the retainer rim 32, and the second adapter portion 50. In the configuration of the adapter 30 depicted in FIGS. 1-2, the first adapter portion 40 functions as an inlet for the liquid flow passage 60, and the second adapter portion 50 functions as an outlet for the liquid flow passage.

Referring to FIGS. 4-7, the retainer rim 32 has a greater diameter than both the first adapter portion 40 and the second adapter portion 50. The diameter of the retainer rim 32 is sized in relation to the bag 20 so that the end margin 28 of the bag may engage securely with the retainer rim and be held by the retainer rim as liquid fills the bag. In some embodiments, the outside edge of retainer rim 32 may have smoothed (e.g., rounded) corners (not shown) to reduce concentrated stress which could cause the bag to tear during installation and/or use. The first adapter portion 40 of the adapter 30 is configured to be attached to the outlet portion 18 of the pump 12. In the illustrated embodiment, an outer portion 42 of the first adapter portion 40 is configured to thread into the outlet portion 18 of the breast pump 12. An interior surface (not shown) of the outlet portion 18 includes mating threads. In the illustrated embodiment, the first adapter portion 40 further includes an unthreaded portion 44 that is connected to the retainer rim 32. It is understood that the unthreaded portion 44 is optional and may not be present in other embodiments. Further, it is understood that in other embodiments the first adapter portion 40 can be attached to the outlet portion 18 by other means such as a snap fit. In the embodiment represented in FIGS. 4-7 the retainer rim 32, the first adapter portion 40, and the second adapter portion 50 are integrally formed as one piece of material. In other embodiments, the retainer rim 32, the first adapter portion 40, and the second adapter portion 50 may be separate pieces that are joined together.

Referring to FIG. 1, when the adapter 30 is attached to the breast pump 12 (i.e., when the first outer portion 42 is threaded into the outlet portion 18 of the breast pump), liquid dispensed from the outlet portion of the breast pump is received in the liquid flow passage 60. The liquid passes through the liquid flow passage 60 and is dispensed from the second adapter portion 50 of the adapter 30. The bag 20 is secured to the adapter 30 so that the liquid dispensed from the second adapter portion 50 of the adapter 30 is received in the bag interior 24.

When the second adapter portion 50 and the retainer rim 32 are inserted in the bag 20, the end margin 28 of the bag body 22 conforms tightly over the outside edge of the retainer rim, securing the bag in place and sealing the end margin of the bag so that only liquid coming from the breast pump 12 can enter the bag. When the bag 20 is thus secured to the adapter 30, the amount of airborne contaminants that can enter the bag is greatly reduced or eliminated. The diameter of the retainer rim 32 corresponds closely to the diameter of the opening in the bag 20. In at least some embodiments, the retainer rim 32 may resiliently deform the bag 20 so that the bag grips the rim securely while milk is being fed into the bag. Although the adapter 30 and bag 20 are sized so that the bag remains in place when filled with liquid, the bag can be detached with minimal resistance, reducing the likelihood of undesired leaks or spills resulting from sudden movements. When the bag 20 is detached from the adapter 30, the bag can be clamped, tied, or otherwise sealed shut, allowing for temporary storage of the liquid in the bag. It is also possible to seal the bag 20 while still on the retainer rim 32 without damaging the bag or making it impossible to remove the bag from the adapter 30.

Figure 4:
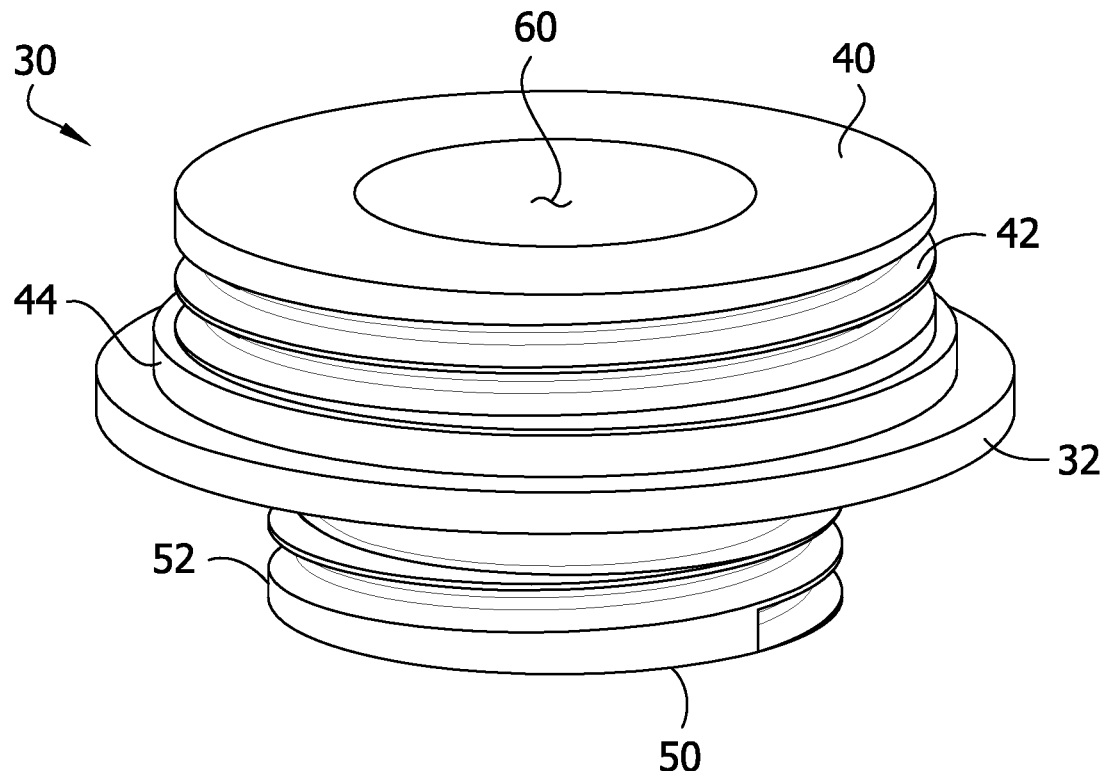
FIG. 4 is a perspective of the adapter.
Figure 5:
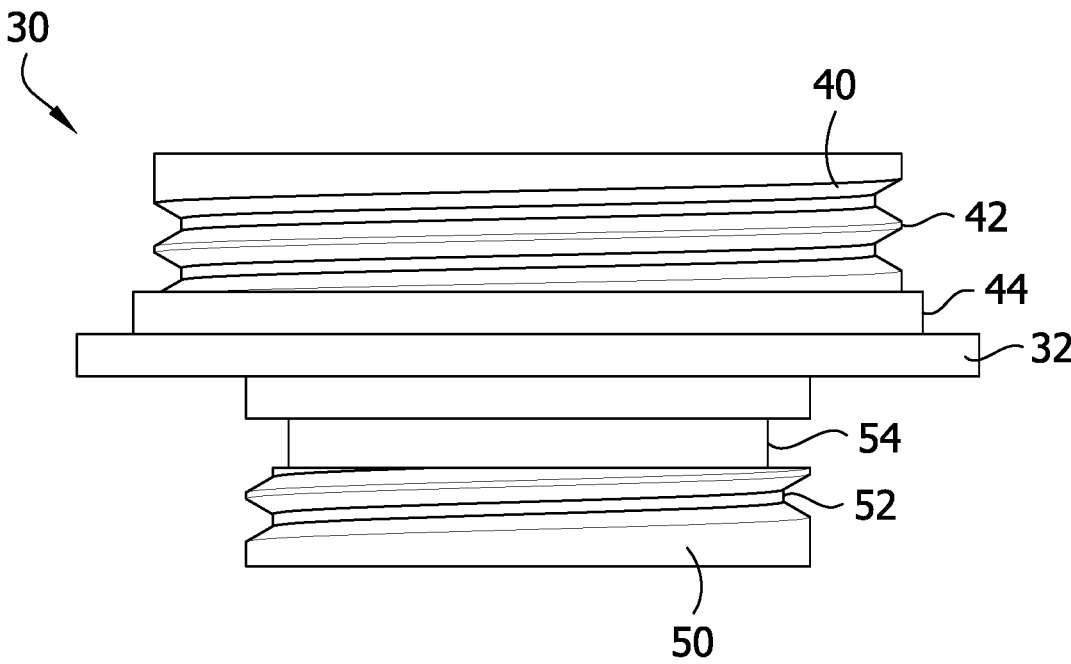
FIG. 5 is a side elevation of the adapter.
Figure 6:
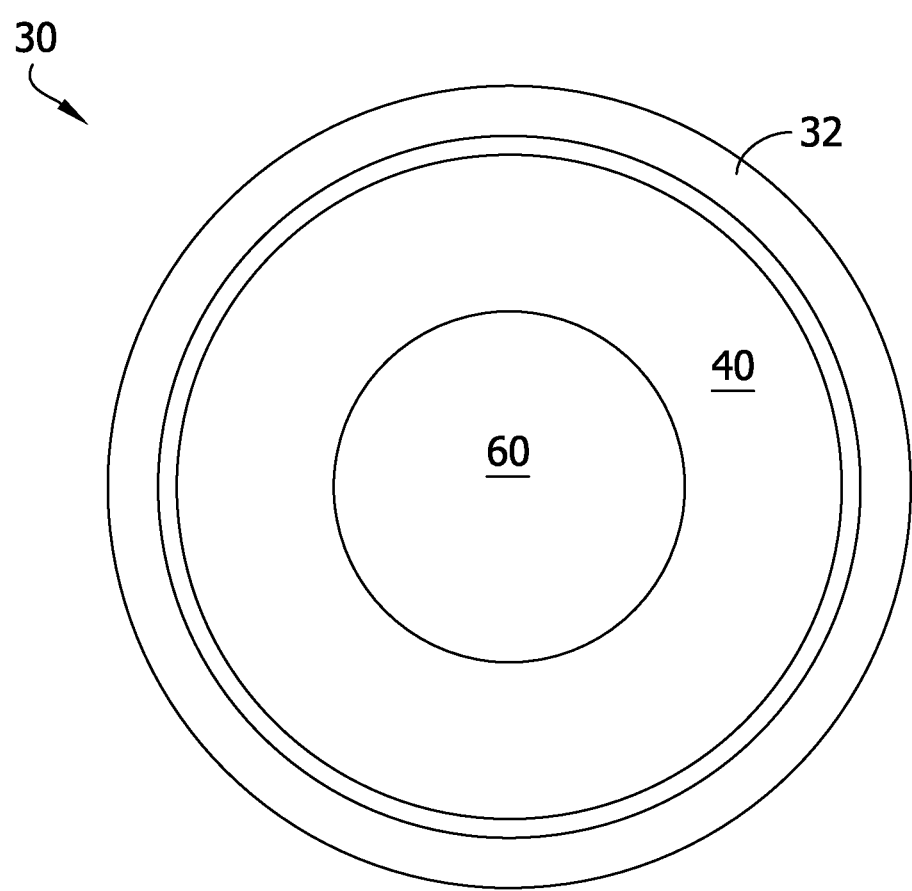
FIG. 6 is a top plan of the adapter.
Figure 7:
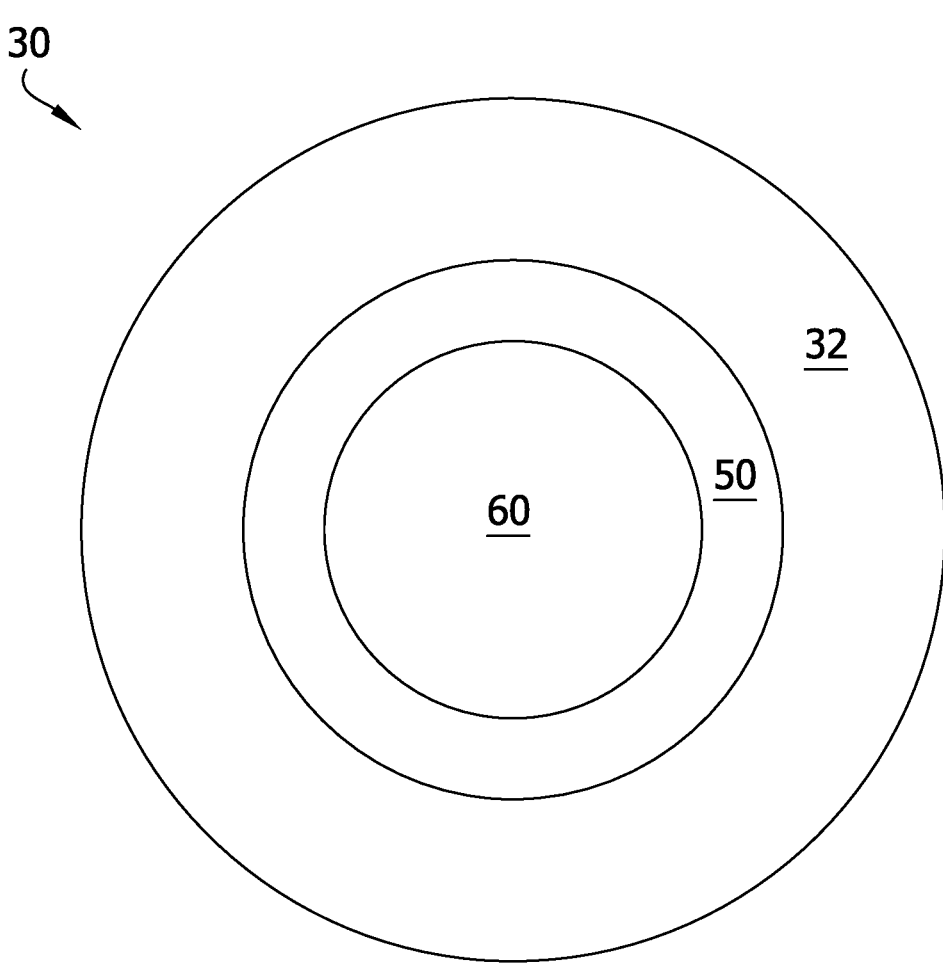
FIG. 7 is a bottom plan of the adapter.
Figure 8:
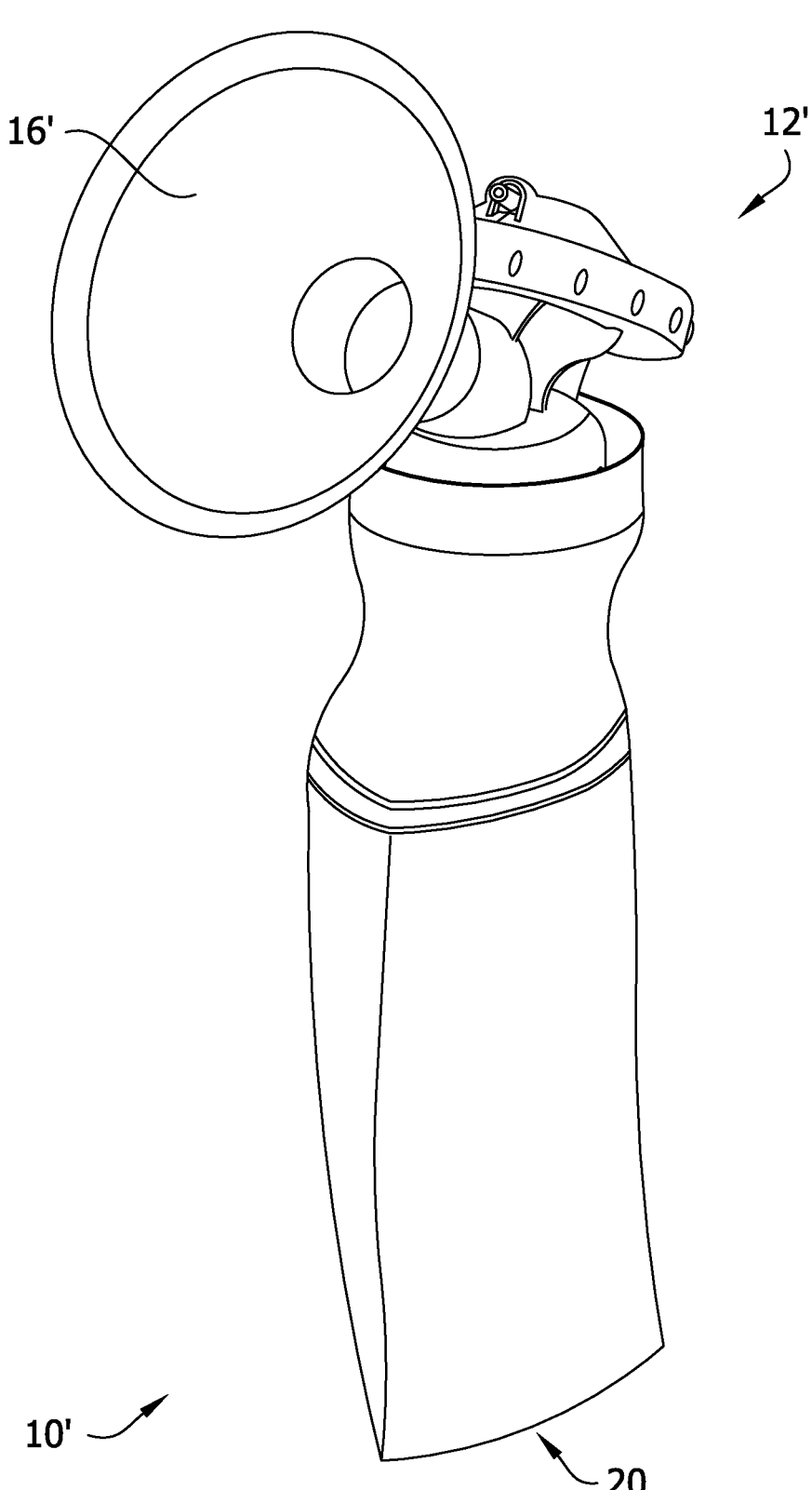
FIG. 8 is a perspective view of another breast pump system with a different breast pump and the breast pump adapter used in an alternative configuration.
Figure 9:
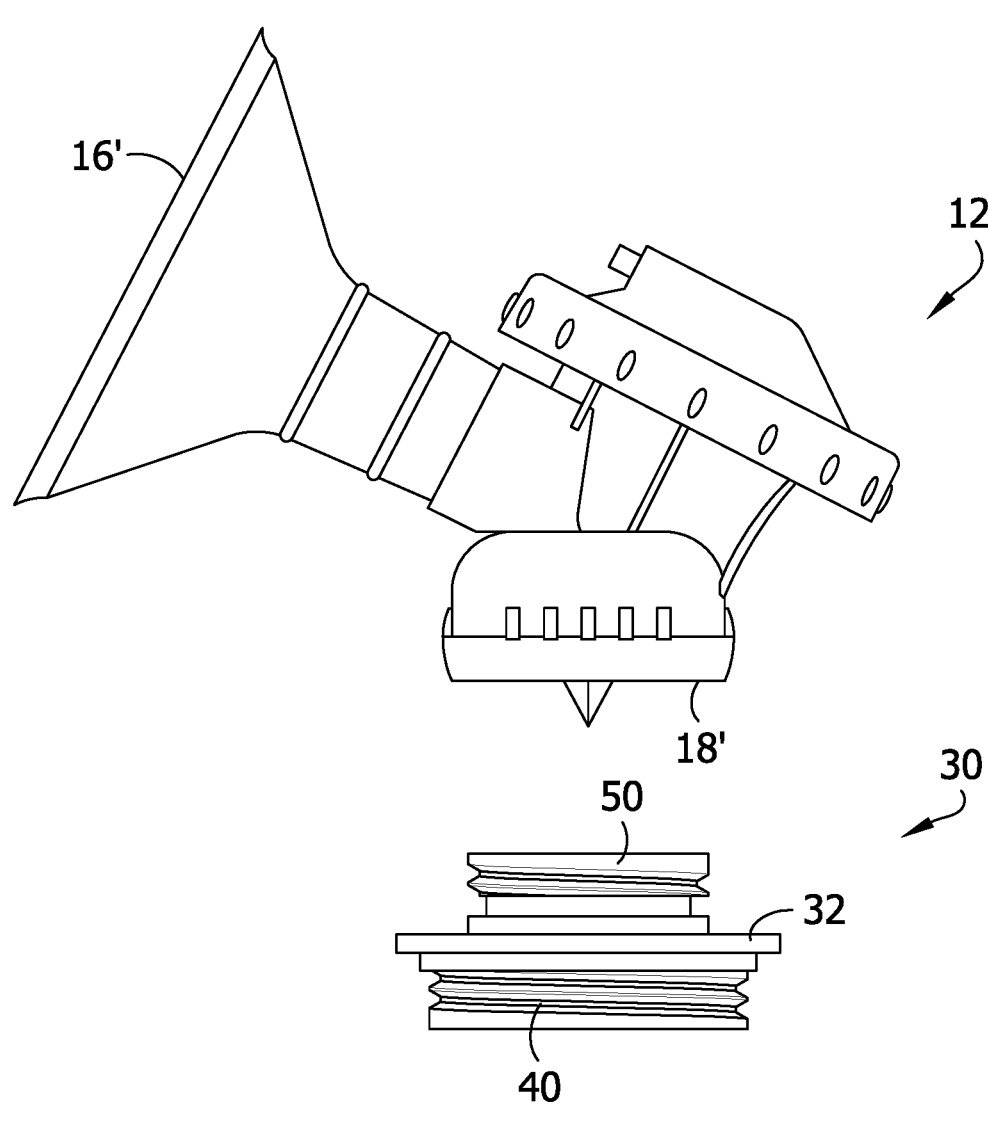
FIG. 9 is an elevation of the alternative breast pump and the adapter from the alternative breast pump system in which the adapter is detached from the alternative breast pump.

Referring to FIGS. 8-9, the breast pump adapter 30 is shown in a second configuration and is attached to a second breast pump 12'. The second configuration of the breast pump adapter 30 can be achieved by inverting the breast pump adapter so the second adapter portion 50 is positioned above the retainer rim 32 and the first adapter portion 40 is positioned beneath the retainer rim. In the second configuration, the second adapter portion 50 functions as an inlet for the liquid flow passage 60, and the first adapter portion 40 functions as an outlet for the liquid flow passage. The second adapter portion 50 of the adapter 30 is configured to be attached to the outlet portion 18' of the pump 12'. Referring to FIGS. 4 and 5, an outer portion 52 of the second adapter portion 50 is configured to thread into the outlet portion 18' of the second breast pump 12'. In the illustrated embodiment, the second adapter portion 50 further includes an unthreaded portion 54 that is connected to the retainer rim 32. It is understood that the unthreaded portion 54 is optional and may not be present in other embodiments. Further, it is understood that in other embodiments the second adapter portion 50 can be attached to the outlet portion 18' by another means such as a snap fit. The breast pump system 10' operates essentially the same as the breast pump system 10 described above in connection with FIG. 1.

In one nonlimiting embodiment, the rim 32 has a diameter of about 64 mm. The first adapter portion 40 has a diameter of about 53 mm and the second adapter portion 50 has a diameter of about 40 mm. The height of the first adapter portion 40 from the upper surface of the rim 32 is about 12.8 mm and the height of the second adapter portion from the lower surface of the rim 32 is about 13.5 mm. The rim 32 is about 3 mm thick. It will be understood that these dimensions are exemplary, but other dimensions may be employed without departing from the scope of the present invention. In general, the first adapter portion 40 and second adapter portions 50 are configured differently so that they can connect to breast pumps having different connection interfaces.

Having described the invention in detail, it will be apparent that modifications and variations to a breast pump adapter system are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements. Additionally, words of position including "above" and "beneath" are intended as relative terms and do not require an element or elements to have an absolute orientation.

In view of the above, it will be seen that the several objects of the invention are achieved and other advantageous results attained.

As various changes could be made in the above product without departing from the scope of the invention, it is intended that all matter contained in the above description and shown in the accompanying drawings shall be interpreted as illustrative and not in a limiting sense.

The invention claimed is:

1. A breast milk pump adapter holding a breast milk collection bag wherein the breast milk pump adapter comprises a retainer engaging and holding the breast milk collection bag on the adapter while the breast milk collection bag is filled with milk by a breast milk pump, the breast milk pump adapter further including a first adapter portion projecting from a first surface of the retainer a first distance and configured for connection to a fitting of a first breast milk pump of a first size, a second adapter portion projecting from a second surface of the retainer opposite the first surface a second distance and configured for connection to a fitting of a second breast milk pump of a second size different from the first size, and a flow passage extending through the first adapter portion, the second adapter portion and the retainer, the retainer having a width which is greater than any width of the adapter away from the retainer, the retainer separating the first adapter portion from the second adapter portion by a separation distance less than one third the lesser of the first distance and the second distance, the breast milk collection bag comprising a body made of flexible material defining an interior and a bag opening, the retainer of the adapter being received in the bag through the bag opening with one of the first adapter portion and second adapter portion projecting outwardly from the bag, the retainer having a peripheral edge engaging the body in the interior of the body to secure the bag to the retainer so that the bag is supported entirely by the retainer when the bag is filled with breast milk.

2. The breast milk pump adapter and breast milk collection bag as set forth in claim 1 wherein the body further comprises an end margin, the retainer of the adapter being engaged with the body in the end margin thereof, the breast milk collection bag including a recloseable seal on the body extending across a width of the bag and constructed to close the interior of the body from the bag opening when closed, the recloseable seal being located at a position spaced from an end of the body including the bag opening.

3. The breast milk pump adapter and breast milk collection bag as set forth in claim 2 wherein the body includes a mark positioned in the end margin to indicate a position of the retainer as received in the bag.

4. The breast milk pump adapter and breast milk collection bag as set forth in claim 1 wherein the retainer is substantially planar in a widthwise direction.

5. The breast milk pump adapter and breast milk collection bag as set forth in claim 1 wherein the first adapter portion comprises an unthreaded portion adjacent to the retainer and a threaded portion on a side of the unthreaded portion opposite the retainer.

6. The breast milk pump adapter and breast milk collection bag as set forth in claim 5 wherein the second adapter portion comprises an unthreaded portion adjacent to the retainer and a threaded portion on a side of the unthreaded portion opposite the retainer.

7. The breast milk pump adapter and breast milk collection bag as set forth in claim 1 wherein the retainer closes the bag opening.

* * * * *